(12) United States Patent
Pan

(10) Patent No.: US 10,881,351 B2
(45) Date of Patent: Jan. 5, 2021

(54) MULTI-SECTION FINGER SLEEVE-TYPE PROBE

(71) Applicant: Weijiang Pan, Guangdong (CN)

(72) Inventor: Weijiang Pan, Guangdong (CN)

( * ) Notice: Subject to any disclaimer, the term of this patent is extended or adjusted under 35 U.S.C. 154(b) by 182 days.

(21) Appl. No.: 16/121,632

(22) Filed: Sep. 5, 2018

(65) Prior Publication Data

US 2018/0368768 A1   Dec. 27, 2018

Related U.S. Application Data

(63) Continuation of application No. PCT/CN2016/094777, filed on Aug. 12, 2016.

(30) Foreign Application Priority Data

Mar. 9, 2016  (CN) ..................... 2016 2 0177873 U

(51) Int. Cl.
*A61B 5/00* (2006.01)
*A61B 5/1455* (2006.01)

(52) U.S. Cl.
CPC ........ *A61B 5/6826* (2013.01); *A61B 5/14552* (2013.01); *A61B 5/6835* (2013.01);
(Continued)

(58) Field of Classification Search
CPC . A61B 5/6826; A61B 5/6835; A61B 5/14552; A61B 5/4818; A61B 2562/16; A61B 2562/0238; A61B 2562/222
See application file for complete search history.

(56) References Cited

U.S. PATENT DOCUMENTS 6,285,895 B1 *  9/2001  Ristolainen ........ A61B 5/14552
                                                      600/310
2001/0045532 A1 * 11/2001  Schulz ................... H01R 12/62
                                                      250/559.4
(Continued)

FOREIGN PATENT DOCUMENTS

CN            1141585 A      1/1997
CN         200939137 Y      8/2007
(Continued)

*Primary Examiner* — Eric F Winakur
*Assistant Examiner* — Abid A Mustansir
(74) *Attorney, Agent, or Firm* — Leong C. Lei

(57) ABSTRACT

The present invention provides a multi-section finger sleeve-type probe, which comprises a finger sleeve body, a flexible flat cable mounted on the finger sleeve body, a light emitting diode, a photo diode, and a wire electrically connected to the flexible flat cable. The finger sleeve body is a cylinder with an opening at the bottom thereof. Comparing with an existing finger sleeve-type probe in which wiring pipes are provided on both the left and right sides of a silicone sleeve and thus the silicone sleeve is flattened, the finger sleeve body fits the shape of a finger and fully wraps around the finger. While being used, the finger is inserted into the finger sleeve body and expands the periphery thereof, thus the finger is totally wrapped to provide a big resistance. The multi-section finger sleeve-type probe can be worn stably, be not easy to drop off, and be suitable for long term use. Also, the finger sleeve body from top to bottom comprises a first knuckle sleeve and a second knuckle sleeve respectively corresponding to the distal knuckle and the medial knuckle of the finger, thus allowing the two knuckles of the finger to be fixed, thereby further increasing the stability of the finger sleeve-type probe when worn.

18 Claims, 4 Drawing Sheets

(52) U.S. Cl.
CPC ..... *A61B 5/4818* (2013.01); *A61B 2562/0238* (2013.01); *A61B 2562/16* (2013.01); *A61B 2562/222* (2013.01)

(56) References Cited

U.S. PATENT DOCUMENTS

| | | | | |
|---|---|---|---|---|
| 2011/0124995 | A1* | 5/2011 | Karma | A61B 5/6838 600/364 |
| 2014/0364705 | A1 | 12/2014 | Parthasarathy | |
| 2016/0228043 | A1* | 8/2016 | O'Neil | A61B 5/14552 |
| 2017/0014075 | A1* | 1/2017 | Morimura | A61B 5/02422 |

FOREIGN PATENT DOCUMENTS

| | | |
|---|---|---|
| CN | 201333039 Y | 10/2009 |
| CN | 103190916 A | 7/2013 |
| CN | 104287746 A | 1/2015 |
| CN | 204218913 U | 3/2015 |
| CN | 104545848 A | 4/2015 |
| CN | 204468058 U | 7/2015 |
| EP | 1491135 A2 | 12/2004 |
| EP | 2327358 A1 | 8/2011 |
| WO | WO2015137151 A1 | 9/2015 |

* cited by examiner

MULTI-SECTION FINGER SLEEVE-TYPE PROBE

CROSS-REFERENCE TO RELATED APPLICATION

This application is a continuing application of PCT Patent Application No. PCT/CN2016/094777 entitled "Multi-Section Finger Sleeve-Type Probe", filed on Aug. 12, 2016, which claims priority to Chinese Patent Application No. 201620177873.4, filed on Mar. 9, 2016, both of which are hereby incorporated in its entireties by reference.

FIELD OF THE INVENTION

The present invention is related to medical devices, particularly related to a multi-section finger sleeve-type probe.

BACKGROUND OF THE INVENTION

Oxygen saturation in blood (known as SpO2) is one of the clinical key physiological parameters. At present, a SpO2 measuring instrument (known as pulse oximeter) using the photoelectric principle is generally used for measurement, and wherein an SpO2 probe, that is, a SpO2 sensor is the core component of the SpO2 measuring instrument.

When using a SpO2 measuring instrument, a normal measuring position is a finger. A SpO2 probe is commonly applied at the finger. The sensor used for the finger is generally a transmission type sensor, that is, a light emitting diode and a photo diode are respectively in contact with the nail and the finger pulp. The light emitted by the light emitting diode passes through the nail and is received by the photo diode on the finger pulp side. When measuring SpO2 in other positions, a reflection type sensor can also be used. Because the blood flow on a finger is rich, the most commonly used measurement position clinically is a finger. The SpO2 probes used for finger measurement according to the composition and use method can be divided into the following types: a finger clip-type SpO2 probe (as shown in CN201079393Y), a finger sleeve-type SpO2 probe (as shown in CN201098122Y), a wrapped type SpO2 probe (as shown in CN301554262), and a paste type SpO2 probe (as shown in CN203169184).

Wherein, in the finger sleeve-type SpO2 probe, a light emitting diode and a photo diode are fixed in a silicone sleeve, and the silicone sleeve is sleeved on the finger during measurement. As shown in FIG. 1 of CN201333039Y, an existing finger sleeve-type SpO2 probe is flat, is narrow on both the up and the down sides, and is wide on both the left and the right sides. When used, it only touches a finger on the finger back and on the finger pulp, and there is a big gap left on both sides of the finger. It is so designed in order to adapt to different shapes and thickness of the fingers of various patients in the hospital, so that it can be worn by the patients without needing many sizes and styles. So, the current market only provides big, medium and small size models, which can be suitable for all adults; the big gap left on the two sides can ensure that when being used by a coma or conscious patient, the accident will not happen, that of being not aware of the blood supply stopped at the distal end of the finger because of the SpO2 probe being too tight. As shown in FIG. 5 of CN201333039Y, in another existing finger sleeve-type SpO2 probe, according to the characteristic of the fingers of most people, that the first knuckle (distal knuckle) is generally thinner than the second knuckle (middle knuckle) and gradually grows from thin to thick, the inner cavity accommodating the finger is enlarged V-shaped from the fingertip to backward, and since the light emitting diode and photo diode are located at the nail of the first knuckle, the wall thickness of the housing wherein is relatively thick. Meanwhile, in order to increase the grip force of the finger sleeve on the finger, as shown in FIG. 1 of CN2785542Y with 150-A and 150-B, the thickness is often increased at the edge of the opening (wherein the finger is inserted) of the finger sleeve, being provided with a lip or a bump; or as shown in FIG. 1 of CN103481443, the thickness on the left and right sides of the finger sleeve is increased to enhance the grip force.

However, these above mentioned designs will cause the following problems. Firstly, the existing finger sleeve-type SpO2 probe is easy to drop off from finger during use, because with the same contact force, the existing finger sleeve-type SpO2 probe only contacts the finger at the finger back and on the finger pulp, and there is a big gap left on both sides of the finger; the finger can move in the left and right directions inside the finger sleeve, and because the contact area is small, the frictional resistance between the finger and the probe is small, it is easy to drop off. Secondly, as shown in FIG. 5 of CN201333039Y and in FIG. 1 of CN2785542Y with150-A, the existing finger sleeve-type SpO2 probe has a small contact area with the finger, and in order to ensure that it is not easy to drop off, the finger sleeve is globally or locally designed to be relatively thick or to be made of a relatively hard material to generate a sufficient elastic force or wrap force, so the pressure on the finger is big, resulting in a bad feeling when wearing the existing finger sleeve-type SpO2 probe. Thirdly, the flat shape will squeeze the two adjacent fingers that are adjacent to the finger wearing the existing finger sleeve-type SpO2 probe, resulting in bad feeling, and the squeeze from time to time may cause the finger sleeve to move and drop off. Fourthly, the existing finger sleeve-type SpO2 probe is on a whole finger section, which is a non-sectioned structure, which does not match the actual segmented fingers. Because the finger back and the finger pulp are pressed by the finger sleeve, equivalently the finger being fixed at a straight position by the finger sleeve, the finger is not easy to bend; common knowledge experience teaches us that the straight finger is easier to drop off from the finger sleeve comparing with a curved finger. Fifthly, as shown with 107A in FIG. 1 of CN201333039Y, due to the wiring pipes of the light emitting diode and photo diode are mainly distributed on the flat sides of the silicone sleeve, so the thickening ridge is required at the wiring pipes. Meanwhile, the internal wiring is a metal wire, which is harder than the silicone, so relatively hard ridge will oppress the fingers on both sides of the finger wearing the existing finger sleeve-type SpO2 probe, resulting in bad feeling. Sixthly, the existing finger sleeve-type SpO2 probe has an opening at the rear end of the finger sleeve for the finger to enter the finger sleeve, and an opening that is not large at the front end for the nail to protrude, and although there are gaps left between the two sides and the finger, the air flow in the gaps is poor; when the use time is long, sweat will remain on the finger contacting the finger sleeve, resulting in bad feeling and being easy to drop off. Seventhly, because the existing finger sleeve is in single section structure, it is difficult to identify that there are two sections of finger are involved during design and use of the probe. In this way, the pressure of the first knuckle and the second knuckle on the finger caused by the probe is the same or similar, and the light emitting diode and photo diode are usually located at the first knuckle. If the pressure on the finger is strengthened by the whole finger sleeve to prevent dropping off, the blood supply of the first knuckle may be weakened, which may affect the measurement. Eighthly, the inner cavity of the existing finger sleeve is V-shaped, of which the front end is small and the back end is large, being similar to the shape of the finger; this design looks ergonomic, but in fact, because each person's finger shape is different, but the thickness of the two knuckles does not change accordingly, there may be some people having a relatively thin second knuckle; in this way, if the existing single section finger sleeve is used, the grip force on the first knuckle is relatively big, and the grip force on the second knuckle is relatively small, so the existing finger sleeve is easy to drop off and the force thereon is uneven, resulting in bad feeling.

Sleep respiration monitoring is an essential measure for the diagnosis, monitoring and treatment of patients with sleep apnea syndrome. Patients on sleep respiration monitoring often need to be monitored during sleeping, and sometimes at home, so there is a high demand for what SpO2 probes to use. During sleeping, the patient's fingers may move involuntarily, which may cause the sensor to drop off and shift, thereby affecting the measurement. If it is applied at home, because there is no guidance from doctors and nurses, how to conveniently and reliably place the finger sleeve-type SpO2 probe is the key of success or failure of measuring. Although the existing finger sleeve-type SpO2 probe can be repeatedly used, it is unreliably fixed on the finger, is easy to drop off during sleeping, has bad feeling during use, and needs to be improved.

SUMMARY OF THE INVENTION

An object of the present invention is to provide a multi-section finger sleeve-type probe with reasonable structure design, being stable and not easy to drop off when worn, and being suitable for long-term use.

To achieve the above mentioned object, the present invention provides a multi-section finger sleeve-type probe, which comprises a finger sleeve body, a flexible flat cable mounted on the inner side of the finger sleeve body, a light emitting diode mounted on the inner side of the finger sleeve body and electrically connected to one end of the flexible flat cable, a photo diode mounted on the inner side of the finger sleeve body and electrically connected to the other end of the flexible flat cable, and a wire with one end thereof electrically connected to the flexible flat cable; and the other end of the wire being used for being electrically connected to an external device.

The finger sleeve body is a cylinder with an opening at the bottom thereof; the multi-section finger sleeve-type probe is worn on a finger through the opening of the bottom of the finger sleeve body, and the front and rear sides of the finger sleeve body respectively correspond to contact the finger back and the finger pulp of the finger, and the left and right sides of the finger sleeve body respectively correspond to contact the left and right sides of the finger; the finger sleeve body correspondingly wraps around the finger, and the finger sleeve body from top to bottom comprises a first knuckle sleeve and a second knuckle sleeve connecting therewith respectively corresponding to the distal knuckle and the medial knuckle of the finger.

Wherein the rear side of the finger sleeve body is provided with a bending structure between the first knuckle sleeve and the second knuckle sleeve, thereby facilitating the bending of the finger when the multi-section finger sleeve-type probe is worn on a finger; the bending structure is a gap, or a groove.

Wherein the inner diameter of the second knuckle sleeve is less than or equal to the inner diameter of the first knuckle sleeve;

wherein, the inner diameter of the second knuckle sleeve refers to an inner diameter when the second knuckle sleeve is expanded into a cylindrical shape without elastic deformation; and the inner diameter of the first knuckle sleeve refers to an inner diameter when the circumferential portion of the first knuckle sleeve at where the light emitting diode and the photo diode are located and the part below the circumferential portion are expanded into a cylindrical shape without elastic deformation.

Wherein the front and rear sides of the finger sleeve body are respectively provided with a mounting groove, and the light emitting diode and the photo diode are fixed in the mounting groove.

Wherein the finger sleeve body is further provided with a wire groove extending from the upper end of the finger sleeve body to both sides of the finger groove body to each mounting groove, and the flexible flat cable is fixed in the wire groove.

Wherein a wire slot is disposed in the front side of the finger sleeve body, which is configured to mount a wire.

Wherein the wire slot extends upward from the lower end of the second knuckle sleeve to the mounting groove at the front side of the first knuckle sleeve.

Wherein the wire slot extends upward from the middle of the second knuckle sleeve to the mounting groove at the front side of the first knuckle sleeve.

Wherein the wire slot extends upward from the first knuckle sleeve to the mounting groove at the front side of the first knuckle sleeve.

Wherein the wall thickness of the left side, the right side, and the rear side of the second knuckle sleeve is uniform.

Wherein the wall thickness of each side of the second knuckle sleeve is uniform.

Wherein the average wall thickness of the left side, the right side, and the rear side of the second knuckle sleeve is 0.01 mm-0.1 mm, 0.1 mm-0.5 mm, or 0.5 mm-1.0 mm.

Wherein the average wall thickness of each side of the second knuckle sleeve is 0.01 mm-0.1 mm, 0.1 mm-0.5 mm, or 0.5 mm-1.0 mm.

Wherein the finger sleeve body has a mounting area and a non-mounting area connected to the mounting area; and the light emitting diode, the photo diode, the flexible flat cable, and the wire are mounted on the mounting area of the finger sleeve body; the average wall thickness of the non-mounted area of the second knuckle sleeve is thinner than or equal to the average wall thickness of the non-mounting area of the first knuckle sleeve.

Wherein the wire groove is disposed at an inner side of the finger sleeve body, and the flexible flat cable is disposed at an inner side of the finger sleeve body.

Wherein the wire groove is disposed at an outer side of the finger sleeve body, and the flexible flat cable is disposed at an outer side of the finger sleeve body.

Wherein the opening of the mounting groove is located inside or outside the finger sleeve body.

Wherein a first window is disposed on the left and right sides of the first knuckle sleeve for increasing the elasticity and air permeability of the finger sleeve body.

Wherein a second window is disposed on the left and right sides of the second knuckle sleeve for increasing the elasticity and air permeability of the finger sleeve body.

Wherein the material of the finger sleeve body is an elastic material.

The multi-section finger sleeve-type probe is used to measure SpO2.

The advantages of the present invention: the present invention provides a multi-section finger sleeve-type probe, which comprises a finger sleeve body, a flexible flat cable mounted on the finger sleeve body, a light emitting diode, a photo diode, and a wire electrically connected to the flexible flat cable. The finger sleeve body is a cylinder with an opening at the bottom thereof. The flexible flat cable crosses the upper end of the sleeve body, and the two ends of the flexible flat cable are respectively located on the front and rear sides of the finger sleeve body corresponding to the finger back and the finger pulp of the finger. The light emitting diode and the photo diode respectively contact the finger back and the finger pulp of the finger. One end of the wire is on the front side of the finger sleeve body to be electrically connected to the flexible flat cable, that is, the pipe wiring connected to the external device on the sleeve body is mainly disposed on the front side. Comparing with an existing finger sleeve-type probe in which wiring pipes are provided on both the left and right sides of a silicone sleeve and thus the silicone sleeve is flattened, the finger sleeve body fits the shape of a finger and fully wraps around the finger. While being used, the finger is inserted into the finger sleeve body and expands the periphery thereof, thus the finger is totally wrapped to provide a big resistance. The multi-section finger sleeve-type probe can be worn stably, be not easy to drop off, and be suitable for long term use. Also, the finger sleeve body from top to bottom comprises a first knuckle sleeve and a second knuckle sleeve respectively corresponding to the distal knuckle and the medial knuckle of the finger, thus allowing the two knuckles of the finger to be fixed, thereby further increasing the stability of the finger sleeve-type probe when worn.

The characteristic and the technical solution of the present invention are best understood from the following detailed description with reference to the accompanying figures, but the figures are only for reference and explaining, not to limit the scope of the invention.

BRIEF DESCRIPTION OF THE DRAWINGS

The technical solution and the beneficial effects of the present invention are best understood from the following detailed description with reference to the accompanying figures and embodiments.

In the figures.

DESCRIPTION OF THE PREFERRED EMBODIMENT

To further set forth the technical solution adopted by the present invention and the effects thereof, the present invention is described detailedly with reference to the following preferred embodiments and the accompanying figures.

Figure 1:
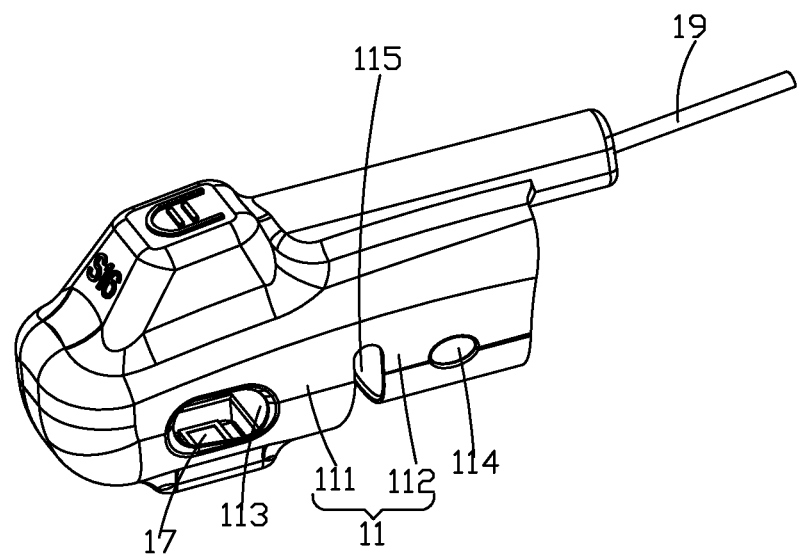
FIG. 1 is a perspective view of a multi-section finger sleeve-type probe of the present invention.
Figure 2:
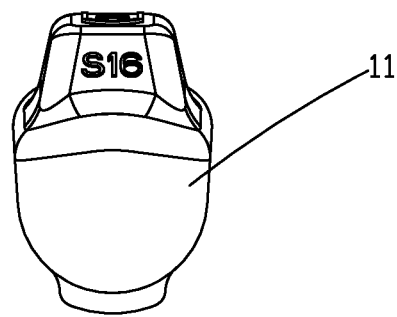
FIG. 2 is a front view of a multi-section finger sleeve-type probe of the present invention.
Figure 3:
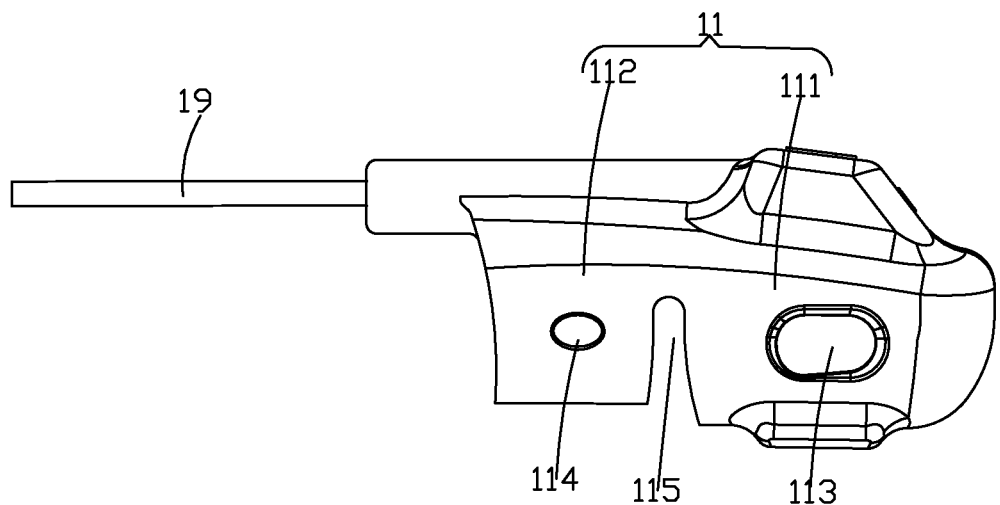
FIG. 3 is a left view of a multi-section finger sleeve-type probe of the present invention.
Figure 4:
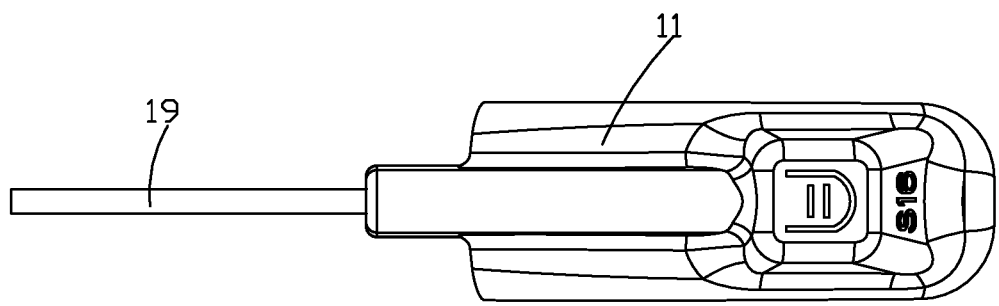
FIG. 4 is a top view of a multi-section finger sleeve-type probe of the present invention.
Figure 5:
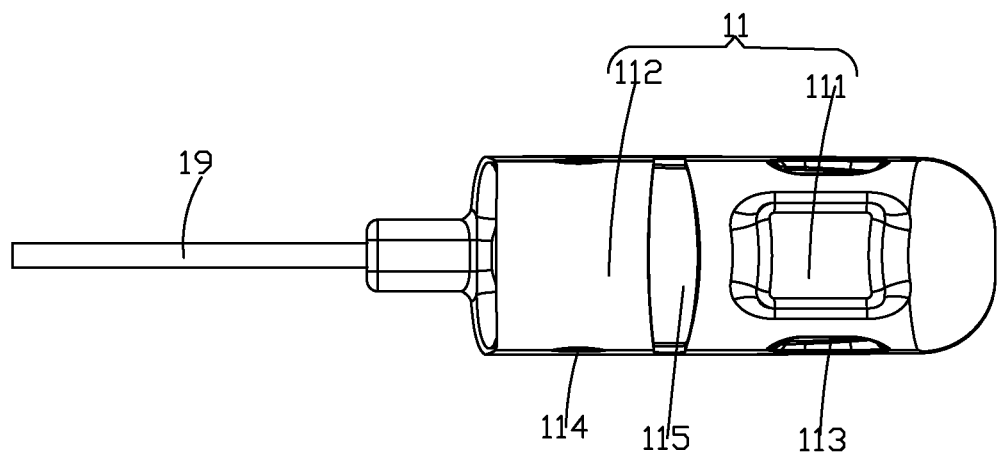
FIG. 5 is a bottom view of a multi-section finger sleeve-type probe of the present invention.
Figure 6:
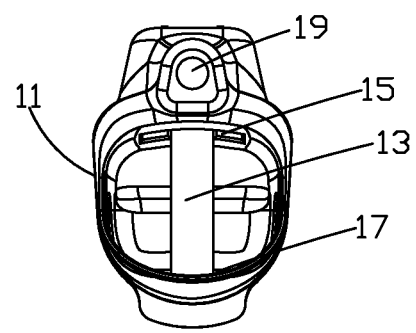
FIG. 6 is a back view of a multi-section finger sleeve-type probe of the present invention.
Figure 7:
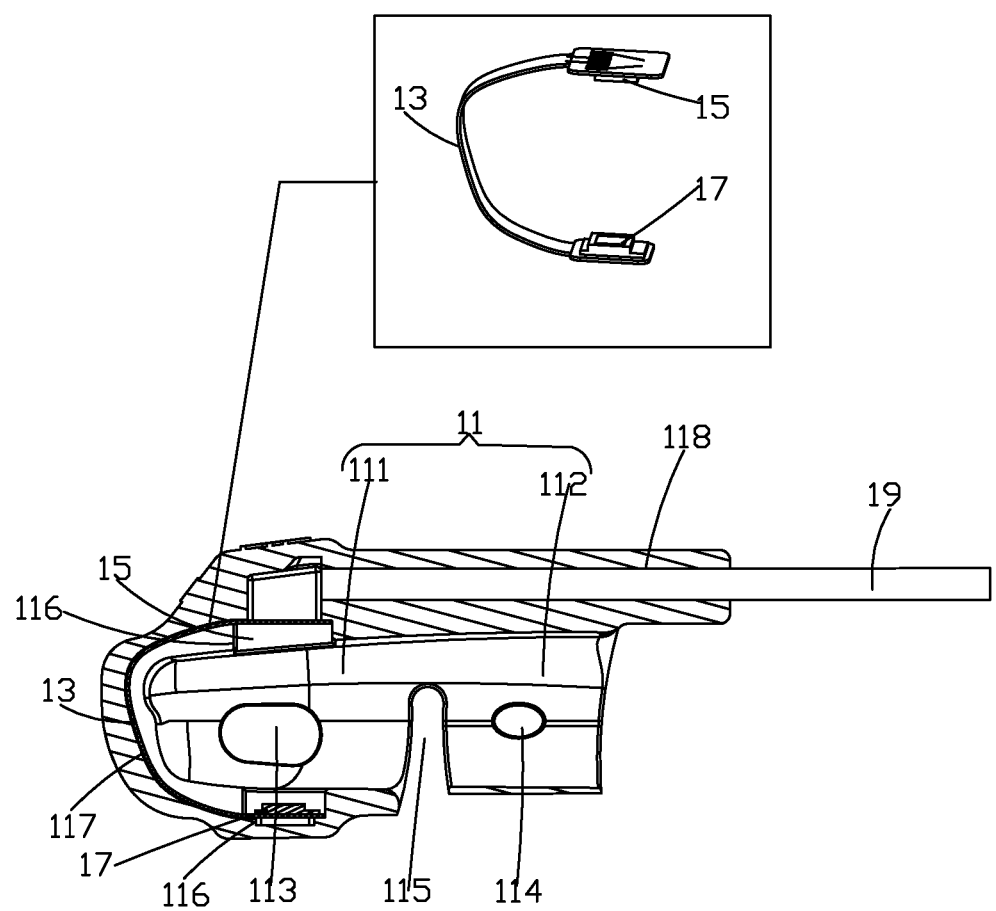
FIG. 7 shows a cross-sectional view of a flexible flat cable wiring in a multi-section finger sleeve-type probe of the present invention, and a stereogram of the flexible flat cable.

Referring from FIG. 1 to FIG. 7, the present invention provides a multi-section finger sleeve-type probe, which comprises a finger sleeve body 11, a flexible flat cable 13 mounted on the finger sleeve body 11, a light emitting diode 15 mounted on the finger sleeve body 11 and electrically connected to one end of the flexible flat cable 13, a photo diode 17 mounted on the finger sleeve body 11 and electrically connected to the other end of the flexible flat cable 13, and a wire 19 with one end thereof electrically connected to the flexible flat cable 13; and the other end of the wire 19 is used for being electrically connected to an external device, so as to connect the finger sleeve-type probe to an external device. The finger sleeve body 11 is a hollow cylindrical integrated structure with a closed upper end and an opening lower end. The finger sleeve-type probe is worn on a finger through the opening of the lower end of the finger sleeve body 11, and the flexible flat cable 13 crosses the upper end of the sleeve body 11 to extend toward the front and rear sides of the finger sleeve body 11. The two ends of the flexible flat cable 13 are respectively located on the front and rear sides of the finger sleeve body 11 corresponding to the finger back and the finger pulp of the finger. The light emitting diode 15 and the photo diode 17 are located at two ends of the flexible flat cable 13 and respectively contact the finger back and the finger pulp of the finger. It is known to those skilled in the art that the light emitting diode 15 can also be located at the finger pulp and the photo diode 17 can also be located at the finger back. One end of the wire 19 is on the front side of the finger sleeve body 11 to be electrically connected to the flexible flat cable 13, that is, the pipe wiring connected to the external device on the sleeve body 11 is mainly disposed on the front side. Comparing with an existing finger sleeve-type probe in which wiring pipes between a light emitting diode and a photo diode are provided on both the left and right sides of a silicone sleeve and thus the silicone sleeve is flattened, the finger sleeve body 11 of the present invention can fit and contact with the finger shape from the periphery of the finger, fully wrap around the finger, and there is no obvious gap around the fingers. While using the finger sleeve-type probe, the finger is inserted into the finger sleeve body and evenly expands the periphery thereof, thus the finger is totally wrapped. Comparing with the existing finger sleeve-type SpO2 probe, the periphery is totally wrapped to increase the contact area, and the frictional resistance between the finger and the probe is increased; it is not easy to drop off, thereby reducing the pressure of the finger sleeve on the finger and increasing the good feeling. The cylindrical design instead of the flat structure design, and with the effect of not squeeze the adjacent fingers of the measured finger, will increases the good feeling. After the finger is inserted, there is no gap between the left and the right sides, and the finger cannot move left and right inside the finger sleeve, thereby being not easy to drop off. It is known to those skilled in the art that, although the finger sleeve body 11 has a hollow cylindrical shape with a closed upper end and an opening lower end, the cross section of the finger sleeve body 11 is not required to be of a typical circular shape, and it may also be of an elliptical shape, be of circular-like shape, or even be of other irregular shapes. The emphasis here of the cylindrical shape is to emphasize that it can tightly wrap around the finger when being used, and the finger can be described as cylindrical. So, the cylindrical shape here corresponds to the cylindrical shape of the finger, and the cylindrical shape is also different from the flat shape of the conventional finger sleeve-type SpO2 probe. When being used, the conventional flat SpO2 probe cannot wrap around the finger even when the finger is inserted therein, and there will be relatively large gaps at the left and right sides. Meanwhile, it is not required that the finger sleeve body 11 must be cylindrical when it is not in use. Because if the finger sleeve body 11 is very thin, it has other shapes even when it is not in use, and it can still tightly wrap around the finger when the finger is inserted therein, to coordinate with the shape of the finger, it can also be called of a cylindrical shape, which is distinguished from the existing flat SpO2 probe, and achieves different using effects. Besides, the present invention does not require that all the cross-sections from the upper end to the lower end of the cylindrical finger sleeve body 11 have the same shape. It is known to those skilled in the art that the multi-section finger sleeve-type probe can be used for measuring SpO2, and can also be used for measuring other physiological parameters, according to the wavelength of the light signal processed by the light emitting diode 15 and the photo diode 17; when the light emitting diode 15 and the photo diode 17 of a suitable wavelength are selected, the multi-section finger sleeve-type probe can be used for measuring SpO2, and other physiological parameters can be measured when the light emitting diode 15 and photo diode 17 of other wavelengths are selected.

Specifically, the finger sleeve body 11 from top to bottom comprises a first knuckle sleeve 111 and a second knuckle sleeve 112 respectively corresponding to the distal knuckle and the middle knuckle of a finger; that is, the length of the finger sleeve body 11 is substantially corresponding to the length of the two knuckles of the finger, thus the two knuckles of the finger can be fixed, further improving the stability of the finger sleeve-type probe when worn; the finger can be freely bent, and it is different in an existing finger sleeve-type SpO2 probe that the finger is fixed at a straight position by the finger sleeve, thereby being easy to drop off.

Specifically, a rear side of the finger sleeve body 11 is provided with a bending structure 115 between the first knuckle sleeve 111 and the second knuckle sleeve 112. The bending structure 115 is a gap, a groove, or the like, which is a structure has an obvious difference in wall thickness, so that when the finger sleeve-type probe is worn on a finger, the first knuckle sleeve 111 and the second knuckle sleeve 112 can be bent in this area, thereby facilitating the bending of the finger, and providing an activity space for the bending of the finger to increase the comfort when wearing; the first knuckle sleeve 111 can be pressed against by the distal knuckle when the finger is bent, and will not easily drop off, thereby avoiding the finger sleeve-type probe dropped off due to the inevitable finger movement of the test subject. The width, length, and the like of the bending structure 115 are determined according to actual effects.

Specifically, the front and rear sides of the finger sleeve body 11 are respectively provided with a mounting groove 116, and the light emitting diode 15 and the photo diode 17 are fixed in the mounting groove 116. Specifically, the light emitting diode 15 and the photo diode 17 are respectively fixed in the mounting groove 116 with a transparent sealant. The finger sleeve body 11 is further provided with a wire groove 117 extending from the upper end of the finger sleeve body 11 to both sides of the finger groove body 11 to each mounting groove 116. The flexible flat cable 13 is fixed in the wire groove 117. Specifically, the flexible flat cable 13 is fixed in the wire groove 117 with a transparent or opaque sealant, which also serves as waterproof protection for the flexible cable 13.

Specifically, the wire groove 117 may be located at the inner side of the finger sleeve body 11 or at the outer side of the finger sleeve body 11. Accordingly, the flexible flat cable 13 may be arranged inside the finger sleeve body 11 or may be arranged outside the finger sleeve body 11.

Specifically, the opening of the mounting groove 116 may be located inside the finger sleeve body 11 or outside the finger sleeve body 11. When the opening of the mounting groove 116 is located outside the finger sleeve body 1, at the groove bottom of the mounting groove 116, that is, the inside of the finger sleeve body 11, a transparent window should be provided to allow red light and infrared light to pass through, so that the light emitting and receiving between the light emitting diode 15 and the photo diode 17 can be realized.

Specifically, a wire slot 118 is disposed in the front side of the finger sleeve body 11. The wire slot 118 is configured to mount a wire 19 electrically connected to one end of the flexible flat cable 13, so that the finger sleeve-type probe is electrically connected to an external device through the wire 19.

Specifically, as known to those skilled in the art, the wire slot 118 can travel over the entire second knuckle sleeve 112, or can only travel a length on the second knuckle sleeve 112, or only travel on the first knuckle 111. Correspondingly, the wire slot 118 may extend upward from the lower end of the second knuckle sleeve 112 to the mounting groove 116 at the front side of the first knuckle sleeve 111, or may extend upward from the middle of the second knuckle sleeve 112 to the mounting groove 116 at the front side of the first knuckle sleeve 111, or may extend upward from the first knuckle sleeve 111 to the mounting groove 116 at the front side of the first knuckle sleeve 111. If the wire slot 118 only travels on the first knuckle sleeve 111, each side of the second knuckle sleeve 112 can have the same wall thickness. If the wire slot 118 partially travels over the second knuckle sleeve 112, the sides of the second knuckle sleeve 112 that do not have the wire slot 118 may have the same wall thickness.

Specifically, in the cylindrical structure of the finger sleeve body 11, except that the front side provided with the wire slot 118 is relatively thick, the other three sides of the second knuckle sleeve 112 have a uniform wall thickness. If the wire slot 118 is not disposed in the second knuckle sleeve 112, the wall thickness of each side of the second knuckle sleeve 112 is uniform. The existing finger sleeve-type SpO2 probe has a local thickness enhancement and wires of the flexible flat cable, the light emitting diode and the photo diode, etc., therefore, the wall thickness of the four sides cannot be uniform. So, when a finger is inserted into the finger sleeve body 11, the second knuckle sleeve 112 has three or four sides that can be evenly expanded to closely wrap the finger. Comparing with the existing finger sleeve-type SpO2 probe which has the upper and lower two sides partially contacting with and wrapping the finger, the multi-section finger sleeve-type probe of the present invention has better feeling and is less likely to drop off. People skilled in the art will recognize that a uniform wall thickness facilitates uniform expansion of the knuckle sleeve as the finger is inserted therein, and increases comfort. The uniform wall thickness here may refer to that, in the area that is randomly designated from the area to be inspected and accounts for 80% thereof (for example, when a certain side is inspected, the area accounting for 80% of the area on the side is taken randomly), the wall thickness difference between the thickest position and the thinnest position of the wall thickness is not more than 50% of the wall thickness of the thickest position. If there is only a small decorative point protrusion on the wall, and it does not significantly affect the uniform expansion of the finger when it is inserted, it can be considered that the position of the protrusion point still has a uniform wall thickness.

Specifically, the finger sleeve body 11 has a mounting area for mounting the light emitting diode 15, the photo diode 17, the flexible flat cable 13, and the wire 19, and a non-mounting area connected to the mounting area; the average wall thickness of the non-mounted area of the second knuckle sleeve 112 may be thinner than the average wall thickness of the non-mounting area of the first knuckle sleeve 111. As is well known in the art, the thinner the silicone finger sleeve is, the better the expandability is, which can be applied to more fingers with different size, and the pressure on the finger is smaller and the comfort is better. Since the first knuckle sleeve 111 is provided with the light emitting diode 15 and the photo diode 17, etc., the front and rear sides of the first knuckle sleeve 111 cannot be made thin; and the second knuckle sleeve 112 does not have these structures, therefore, it can be made thinner than the first knuckle sleeve 111; so that the second knuckle sleeve 112 has the effect to fix the finger sleeve on the finger, and the first knuckle sleeve 111 only has the effect of measurement. The existing finger-type SpO2 probe has only one section, and it needs to ensure sufficient grip force, so the wall thickness cannot be made very thin; without consideration of the wall thickness of the light emitting diode, the photo diode, and the wire, the average wall thickness of other parts is at least 1 mm.

Specifically, the average wall thickness of the side with no wire slot of the second knuckle sleeve 112 of the finger sleeve body 11 may be 0.01 mm-0.1 mm.

Specifically, the average wall thickness of the side with no wire slot of the second knuckle sleeve 112 of the finger sleeve body 11 may also be 0.1 mm-0.5 mm.

Specifically, the average wall thickness of the side with no wire slot of the second knuckle sleeve 112 of the finger sleeve body 11 may also be 0.5 mm-1.0 mm.

Specifically, the inside diameter of the second knuckle sleeve 112 of the finger sleeve body 11 may be decreased. The inner diameter herein refers to an index for measuring the size of the inner cavity in which the first knuckle sleeve 111 and the second knuckle sleeve 112 accommodate a finger. Since the two knuckle sleeves are not typically cylindrical, the inner diameter is not the diameter of a particular cross section. If it needs to be measured by a certain measurement method, a cylindrical simulated finger with a variable diameter can be inserted into the first knuckle sleeve 111 and the second knuckle sleeve 112 respectively. Increasing the diameter of the cylindrical simulated finger gradually, until the first knuckle sleeve 111 and the second knuckle sleeve 112 are just opened, and at this moment the first knuckle sleeve 111 and the second knuckle sleeve 112 are just tightly wrapped around and contact with the circumference of the cylindrical simulated finger without generating significant pressure to the finger thereon. In other words, at this moment the first knuckle sleeve 111 and the second knuckle sleeve 112 are only expanded by the simulated finger into a cylindrical shape without significant stretched, and the diameters of the cylindrical simulated finger measured at this moment can be considered to be the inner diameter of the first knuckle sleeve 111 and the inner diameter of the second knuckle sleeve 112. Meanwhile, since the inner cavity of the first knuckle sleeve 111 is not equal from top to bottom, the portion measured by the simulated finger herein refers to the part between the circumferential portion of the first knuckle sleeve 111 at where the light emitting diode 15 and the photo diode 17 are located, and the bending structures 115; the front end portion of the first knuckle sleeve 111 generally tends to be shrunk to fit the shape of the finger and has little effect on finger fixation, and thus is not an indicator for measuring the size of the first knuckle sleeve 111. People skilled in the art know that the smaller the inner diameter of the silicone finger sleeve is, the tighter the finger is wrapped, and the less easily the finger sleeve is to drop off, but the pressure on the finger also becomes bigger. Usually, the first knuckle is thinner than the second knuckle of the finger, and is V-shaped, therefore, when the existing finger sleeve is designed, the inner cavity gap of the first knuckle is smaller than the inner cavity gap of the second knuckle. That is to say, from the inside, the inner cavity gap of the existing finger sleeve gets smaller and smaller toward the fingertips, so that the finger is more evenly stressed. Since each person's fingers are different, it is only theoretically possible to achieve the entire finger to be evenly stressed. In fact, because the relative dimensions of the first knuckle and the second knuckle are difficult to be proportional, the existing finger sleeve may have a large force on the front end of the finger and a small force on the second knuckle, which is easy to drop off, and also affects the measurement. In the present invention, when the pressure on the finger is reduced as the thickness of the second knuckle sleeve 112 of the finger sleeve body 11 is reduced, the inner diameter of the second knuckle sleeve 112 can be relatively reduced, that is, the inner diameter of the second knuckle sleeve 112 can be made equal to or even smaller than that of the first knuckle sleeve 111, and the longitudinal section of the inner cavity accommodating the finger can be U-shaped instead of being usually V-shaped when viewed from the front towards the rear.

Specifically, the two ends of the flexible flat cable 13 are respectively located at the front and rear sides of the first knuckle sleeve 111, and the light emitting diode 15 and the photo diode 17 are located at two ends of the flexible flat cable 13 and are respectively in contact with the finger nail and finger pulp of a finger. Since the two sides of the finger have no flexible flat cable, the problem that the relatively hard ridge of the existing finger sleeve-type SpO2 probe when worn will occupy the position of the adjacent fingers, and result in bad feeling, is solved.

Specifically, a first window 113 is disposed on the left and right sides of the first knuckle sleeve 111. Further, a second window 114 is disposed on the left and right sides of the second knuckle sleeve 112. The first window 113 and the second window 114 increase the elasticity of the finger sleeve body 11 to prevent the finger from being too tightly fixed in the finger sleeve body 11. In addition, the windows increase the air permeability of the finger sleeve, and solve the problem that when using the existing finger sleeve-type SpO2 probe for a long time, it is easy to generate sweat due to poor air permeability, thereby improving the wearing comfort of the finger sleeve.

Specifically, the material of the finger sleeve body 11 is an elastic material such as silicone, rubber or the like.

In summary, the present invention provides a multi-section finger sleeve-type probe, which comprises a finger sleeve body, a flexible flat cable mounted on the finger sleeve body, a light emitting diode, a photo diode, and a wire electrically connected to the flexible flat cable. The finger sleeve body is a cylinder with an opening at the bottom thereof. The flexible flat cable crosses the upper end of the sleeve body, and the two ends of the flexible flat cable are respectively located on the front and rear sides of the finger sleeve body corresponding to the finger back and the finger pulp of the finger. The light emitting diode and the photo diode respectively contact the finger back and the finger pulp of the finger. One end of the wire is on the front side of the finger sleeve body to be electrically connected to the flexible flat cable, that is, the pipe wiring connected to the external device on the sleeve body is mainly disposed on the front side. Comparing with an existing finger sleeve-type probe in which wiring pipes are provided on both the left and right sides of a silicone sleeve and thus the silicone sleeve is flattened, the finger sleeve body fits the shape of a finger and fully wraps around the finger. While being used, the finger is inserted into the finger sleeve body and expands the periphery thereof, thus the finger is totally wrapped to provide a big resistance. The multi-section finger sleeve-type probe can be worn stably, be not easy to drop off, and be suitable for long term use. Also, the finger sleeve body from top to bottom comprises a first knuckle sleeve and a second knuckle sleeve respectively corresponding to the distal knuckle and the medial knuckle of the finger, thus allowing the two knuckles of the finger to be fixed, thereby further increasing the stability of the finger sleeve-type probe when worn.

Although the present invention has been described in detail with above said embodiments, but it is not to limit the scope of the invention. So, all the modifications and changes according to the characteristic and spirit of the present invention, are involved in the protected scope of the invention.

What is claimed is:

1. A multi-section finger sleeve-type probe comprising a finger sleeve body, a flexible flat cable mounted on the finger sleeve body, a light emitting diode mounted on the finger sleeve body and electrically connected to one end of the flexible flat cable, a photo diode mounted on the finger sleeve body and electrically connected to the other end of the flexible flat cable, and a wire with one end thereof electrically connected to the flexible flat cable; the other end of the wire being used for being electrically connected to an external device;

the finger sleeve body being cylindrical with an opening at the bottom thereof; the multi-section finger sleeve-type probe being configured to be worn on a finger through the opening of the bottom of the finger sleeve body, the front and rear sides of the finger sleeve body being respectively configured to fully contact the finger back and the finger pulp of the finger, and the left and right sides of the finger sleeve body being respectively configured to fully contact the left and right sides of the finger; the finger sleeve body being configured to wrap around all sides of the finger, the finger sleeve body from top to bottom comprising a first knuckle sleeve and a second knuckle sleeve connecting therewith respectively configured to correspond to the distal knuckle and the medial knuckle of the finger;

wherein the rear side of the finger sleeve body is provided with a bending structure between the first knuckle sleeve and the second knuckle sleeve, thereby facilitating the bending of the finger when the multi-section finger sleeve-type probe is worn on a finger; the bending structure is a gap, or a groove.

2. The multi-section finger sleeve-type probe of claim 1, wherein the inner diameter of the second knuckle sleeve is less than or equal to the inner diameter of the first knuckle sleeve;

wherein, the inner diameter of the second knuckle sleeve refers to an inner diameter when the second knuckle sleeve is expanded into a cylindrical shape without elastic deformation; and the inner diameter of the first knuckle sleeve refers to an inner diameter when the circumferential portion of the first knuckle sleeve at where the light emitting diode and the photo diode are located and the part below the circumferential portion are expanded into a cylindrical shape without elastic deformation.

3. The multi-section finger sleeve-type probe of claim 1, wherein the front and rear sides of the finger sleeve body are respectively provided with a mounting groove, and the light emitting diode and the photo diode are fixed in the mounting groove.

4. The multi-section finger sleeve-type probe of claim 3, wherein the finger sleeve body is further provided with a wire groove extending from the upper end of the finger sleeve body to both sides of the finger sleeve body and to each mounting groove, and the flexible flat cable is fixed in the wire groove.

5. The multi-section finger sleeve-type probe of claim 3, wherein a wire slot is disposed in the front side of the finger sleeve body for mounting the wire.

6. The multi-section finger sleeve-type probe of claim 5, wherein the wire slot extends upward from the lower end of the second knuckle sleeve to the mounting groove at the front side of the first knuckle sleeve.

7. The multi-section finger sleeve-type probe of claim 5, wherein the wire slot extends upward from the middle of the second knuckle sleeve to the mounting groove at the front side of the first knuckle sleeve.

8. The multi-section finger sleeve-type probe of claim 5, wherein the wire slot extends upward from the first knuckle sleeve to the mounting groove at the front side of the first knuckle sleeve.

9. The multi-section finger sleeve-type probe of claim 6, wherein the wall thickness of the left side, the right side, and the rear side of the second knuckle sleeve is uniform, the average wall thickness of the left side, the right side, and the rear side of the second knuckle sleeve is 0.01 mm-0.1 mm, 0.1 mm-0.5 mm, or 0.5 mm-1.0 mm.

10. The multi-section finger sleeve-type probe of claim 8, wherein the wall thickness of each side of the second knuckle sleeve is uniform, the average wall thickness of each side of the second knuckle sleeve is 0.01 mm-0.1 mm, 0.1 mm-0.5 mm, or 0.5 mm 1.0 mm.

11. The multi-section finger sleeve-type probe of claim 7, wherein the wall thickness of the left side, the right side, and the rear side of the second knuckle sleeve is uniform, the average wall thickness of the left side, the right side, and the rear side of the second knuckle sleeve is 0.01 mm-0.1 mm, 0.1 mm-0.5 mm, or 0.5 mm-1.0 mm.

12. The multi-section finger sleeve-type probe of claim 1, wherein the finger sleeve body has a mounting area and a non-mounting area connected to the mounting area; the light emitting diode, the photo diode, the flexible flat cable, and the wire are mounted on the mounting area of the finger sleeve body; the average wall thickness of the non-mounted area of the second knuckle sleeve is thinner than or equal to the average wall thickness of the non-mounting area of the first knuckle sleeve.

13. The multi-section finger sleeve-type probe of claim 4, wherein the wire groove is disposed at an inner side of the finger sleeve body, and the flexible flat cable is disposed at an inner side of the finger sleeve body.

14. The multi-section finger sleeve-type probe of claim 4, wherein the wire groove is disposed at an outer side of the finger sleeve body, and the flexible flat cable is disposed at an outer side of the finger sleeve body.

15. The multi-section finger sleeve-type probe of claim 1, wherein a first window is disposed on the left and right sidewalls of the first knuckle sleeve for increasing the elasticity and air permeability of the finger sleeve body.

16. The multi-section finger sleeve-type probe of claim 15, wherein a second window is disposed on the left and right sidewalls of the second knuckle sleeve for increasing the elasticity and air permeability of the finger sleeve body.

17. The multi-section finger sleeve-type probe of claim 1, wherein the material of the finger sleeve body is an elastic material.

18. The multi-section finger sleeve-type probe of claim 1, being configured to measure oxygen saturation in blood.

* * * * *